US006482636B1

(12) United States Patent
Donovan et al.

(10) Patent No.: US 6,482,636 B1
(45) Date of Patent: Nov. 19, 2002

(54) **CONSTRUCTED *BACILLUS THURINGIENSIS* STRAINS PRODUCING MOSQUITOCIDAL CRYSTAL PROTEINS**

(75) Inventors: William P. Donovan, Manchester, MO (US); James A. Baum, Webster Groves, MO (US)

(73) Assignee: Certis USA, L.L.C., Columbia, MD (US)

( * ) Notice: Subject to any disclaimer, the term of this patent is extended or adjusted under 35 U.S.C. 154(b) by 0 days.

(21) Appl. No.: 09/373,257

(22) Filed: Aug. 12, 1999

(51) Int. Cl.$^7$ .......................... C12N 1/21; C12N 1/20; C12N 15/63; C12N 15/75
(52) U.S. Cl. .............................. 435/252.31; 435/320.1; 435/252.3; 435/252.5
(58) Field of Search .................. 435/252.31, 252.5, 435/320.1, 252.3

(56) References Cited

U.S. PATENT DOCUMENTS

| | | | |
|---|---|---|---|
| 4,935,353 A | 6/1990 | Burges et al. | 435/69.1 |
| 5,080,897 A | 1/1992 | Gonzalez, Jr. et al. | 424/93.2 |
| 5,441,884 A | 8/1995 | Baum | 435/252.31 |

OTHER PUBLICATIONS

Angsuthanasombat et al., "Comparison of *Bacillus thuringiensis* subsp. *Israelensis* CryIVA and CryIVB cloned toxins reveals synergism in vivo," *FEMS Microbiol. Letts.*, 1992, 94, 63–68.
Bar et al., "Cloning and Expression of *Bacillus thuringiensis israelensis* δEndotoxin DNA in *B. sphaericus,*" *J. Invert. Pathology*, 1991, 57, 149–158.
Belliveau et al., "Transformation of *Bacillus cereus* Vegetative Cells by Electroporation," *App. Environ. Microbiol.*, 1989, 55(6), 1649–1652.
Crickmore et al., "Revision of the Nomenclature of the *Bacillus thuringiensis* Pesticidal Crystal Proteins," *Microbiol. Molec. biol. Rev.*, 1998, 62(3), 807–813.
Daum, "Revision of Two Computer Programs for Probit Analysis," *Bull. Entomol. Soc. Am.*, 1970, 16, 10–15.
DeBarjac et al., "Classification of *Bacillus thuringiensis* Strains," *Entomophaga*1990, 35(2), 233–240.
Donovan et al., "Molecular Characterization of a Gene Encoding a 72–Kilodalton Mosquito–Toxic Crystal Protein from *Bacillus thuringiensis* subsp. *Israelensis*," *J. Bacteriol.*, 1988, 170(10), 4732–4738.
González et al., "Plasmid Transfer in *Bacillus thuringiensis*," in *Genetic Exchange*, Streips, U.N. et al. (eds.), Marcel Dekker, Inc., New York, 1982, p. 85–95.
González et al., "A Large Transmissible Plasmid is Required for Crystal Toxin Production in *Bacillus thuringiensis* Variety I*israelensis*," *Plasmid*, 1984, 11, 28–38.
González Jr. et al., "Transfer of *Bacillus thuringiensis* plasmids coding for δ–endotoxin among strains of *B. Thuringiensis* and *B. Cereus*", *Proc. Natl. Acad. Sci USA*, 1982, 79, 6951–6955.

Hófte et al., "Insecticial Crystal Proteins of *Bacillus thuringiensis,*" *Microbiol. Rev.*, 1989, 53(2), 242–255.
Jensen et al., "The Aggregation–Mediated Conjugation System of *Bacillus thuringiensis* subsp. *Israelensis*: Host Range and Kinetics of Transfer," *Current Microbiol.*, 1996, 33, 228–236.
Kawalek et al., "Isolation and Identification of Novel Toxins from a New Mosquitocidal Isolate from Malaysia, *Bacillus thuringiensis* subsp. *Jegathesan,*" *Appl. Environ. Microbiol.*, 1995, 61(8), 2965–2969.
Muthukumar et al., "The Glycoprotein Toxin of *Bacillus thuringiensis* subsp. *Israelensis* Indicates a Lectinlike Receptor in the Larval Mosquito Gut,"*App. Environ. Microbiol.*, 1987, 53(11), 2650–2655.
Pfannenstiel et al., "Amino Sugars in the Glycoprotein Toxin from *Bacillus thuringiensis* subsp. *Israelensis,*" *J. Bacteriol.*, 1987, 169(2), 796–801.
Sekar et al., "Molecular cloning of the delta–endotoxin gene of *Bacillus thuringiensis* var. *israelensis,*" *Gene*, 1985, 33, 151–158.
Southern, "Detection of Specific Sequences Among DNA Fragments Separated by Gel Electrophoresis," *J. Mol. Biol.*, 1975, 98, 503–517.
Trisrisook et al., "Molecular Cloning of the 130–Kilodalton Mosquitocidal δ–Endotoxin Gene of *Bacillus thuringiensis* subsp. *Israelensis* in *Bacillus sphaericus,*" *Appl. Envir. Microbiol.*, 1990, 56(6), 1710–1716.
Wu et al., "Synerigsm of mosquitocidal toxicity between CytA and CryIVD proteins using inclusions produced from cloned genes of *Bacillus thuringiensis,*" *Molec. Microbiol.*, 1994, 13(6), 965–972.

*Primary Examiner*—Gabriele Bugaisky
(74) *Attorney, Agent, or Firm*—Akin, Gump, Strauss, Hauer & Feld, L.L.P.

(57) ABSTRACT

The present invention provides constructed *Bacillus thuringiensis* (*B.t.*) strains that are toxic to mosquito larvae. The mosquito-toxic *B.t.* strains have improved characteristics, such as increased production of mosquito-toxic proteins, reduced number of spores or increased variety of mosquito-toxic proteins, compared with the well-known, mosquito-toxic strain *Bacillus thuringiensis* subspecies *israelensis* (*B.t. israelensis*). The present invention involves insertion of an antibiotic-resistance gene into the *B.t. israelensis* mosquito-toxin plasmid having a size of approximately 75 mDa such that the plasmid is "tagged" with antibiotic resistance. The advantage of the tagged mosquito-toxin plasmid is that it permits detection of the rare event in which the mosquito-toxin plasmid is transferred from the *B.t. israelensis* strain (the donor strain) into a non-*B.t. israelensis* strain (the recipient strain) that normally does not harbor the mosquito-toxin plasmid. Non-*B.t. israelensis* recipient cells may have improved characteristics such as reduced spore numbers or increased variety of mosquito-toxic proteins. The present invention also provides for a mechanism of inactivating the antibiotic tag so that *B.t.* strains harboring the mosquito-toxin plasmid do not disseminate antibiotic resistance when released into the environment.

19 Claims, No Drawings

CONSTRUCTED *BACILLUS THURINGIENSIS* STRAINS PRODUCING MOSQUITOCIDAL CRYSTAL PROTEINS

FIELD OF THE INVENTION

The present invention relates to constructed bacterial strains that produce mosquito-toxic proteins. Compared with the highly mosquito-toxic strain *B.t. israelensis*, the constructed strains have improved characteristics, such as reduced spore number or increased variety of mosquito-toxic proteins. The invention also relates to a method of constructing improved mosquito-toxic strains of bacteria wherein the mosquito-toxin plasmid of *B.t. israelensis* is tagged with an antibiotic-resistance gene, thus permitting the detection of transfer of the mosquito-toxin *B.t. israelensis* plasmid from a donor bacteria strain into a recipient bacteria strain.

BACKGROUND OF THE INVENTION

*Bacillus thuringiensis* (*B.t.*) is a gram-positive bacterium that produces proteinaceous crystalline inclusions during sporulation. These *B.t.* crystal proteins are often highly toxic to specific insects. Insecticidal activity has been identified for crystal proteins from various *B.t.* strains against insect larvae from the insect orders Lepidoptera (caterpillars), Diptera (mosquitos, flies) and Coleoptera (beetles).

Individual *B.t.* crystal proteins, also called delta-endotoxins or parasporal crystals or toxin proteins, can differ extensively in their structure and insecticidal activity. These insecticidal proteins are encoded by genes typically located on large plasmids, greater than 30 megadaltons (mDa) in size, that are found in *B.t.* strains. A number of these *B.t.* toxin genes have been cloned and the insecticidal crystal protein products characterized for their specific insecticidal properties. Hofte et al. provides a review of cloned *B.t.* toxin genes and crystal proteins (*Microbiol. Rev.*, 1989, 53, 242–255).

The insecticidal properties of *B.t.* have long been recognized and *B.t.* strains have been incorporated into commercial biological insecticide products for over forty years. Commercial *B.t.* insecticide formulations typically contain dried *B.t.* fermentation cultures whose crystal protein is toxic to various insect species.

Traditional commercial *B.t.* bioinsecticide products are derived from "wild-type" *B.t.* strains, i.e., purified cultures of *B.t.* strains isolated from natural sources. Newer commercial *B.t.* bioinsecticide products are based on genetically altered *B.t.* strains, such as the transconjugant *B.t.* strains described in U.S. Pat. No. 5,080,897, issued Jan. 14, 1992, and U.S. Pat. No. 4,935,353, issued Jun. 19, 1990.

Various *B.t.* strains have been classified based on the reaction of the *B.t.* flagella with antibodies. A *B.t.* strain whose flagella react with a unique antibody is classified as a unique serovar, and over thirty different *B.t.* serovars or subspecies have been described (DeBarjac and Frachon, *Entomophaga*, 1990, 35, 233–240). Each *B.t.* subspecies often produces unique types of insecticidal crystal proteins. For example, *B.t.* subspecies *kurstaki* produces crystal proteins of approximatley 130 kilodaltons (kD) and 70 kD in size that are toxic to caterpillars, whereas *B.t.* subspecies *tenebrionis* produces a crystal protein of 72 kD which is toxic to beetles.

*B.t.* subspecies *israelensis* (*B.t. israelensis*) is a mosquito-toxic bacterium that produces at least four crystal proteins designated Cry4A, Cry4B, Cry4D and CytA that have been shown to be toxic to mosquito larvae. The *B.t.* crystal toxin gene designations have recently been revised (Crickmore et al., *Microbiol. Molec. Biol. Rev.*, 1998, 62, 807–813). *B.t. israelensis* contains several native plasmids of approximate sizes 3.3, 4.2, 4.9, 10.6, 68, 75, 105 and 135 mDa (Gonzalez and Carlton, *Plasmid*, 1984, 11, 28–38). The genes for the Cry4A, Cry4B, Cry4D and CytA proteins are all carried on a single large plasmid, the mosquito-toxin plasmid, of approximately 75 mDa in *B.t. israelensis* (Gonzalez and Carlton, *Plasmid*, 1984, 11, 28–38). Gene cloning experiments have shown that recombinant non-*B.t. israelensis* bacteria containing cloned *B.t. israelensis* mosquito-toxin genes are generally less toxic to Aedes aegypti mosquitos than wild-type *B.t. israelensis* (Sekar and Carlton, *Gene*, 1985, 33, 151–158; Donovan et al., *J. Bacteriol.*, 1988, 170, 4732–4738; Trisrisook et al., *Appl. Envir. Microbiol.*, 1990, 56, 1710–1716; Bar et al., *J. Invert. Pathology*, 1991, 57, 149–158; Angsuthanasombat et al., *FEMS Microbiol. Letts.*, 1992, 94, 63–68; Wu et al., *Molec. Microbiol.*, 1994, 13, 965–972).

One explanation for the reduced mosquito toxicity seen with recombinant bacteria containing cloned *B.t. israelensis* mosquito-toxin-genes compared with wild-type *B.t. israelensis* is that all four *B.t. israelensis* crystal protein genes (i.e., cry4A, cry4B, cry4D and cytA) must be present in the same cell for maximum mosquito toxicity. Other factors of *B.t. israelensis* also contribute to its mosquito toxicity. For example, *B.t. israelensis* produces specific sugar residues that are attached to the *B.t. israelensis* crystal proteins (Pfannenstiel et al., *J. Bacteriol.*, 1987, 169, 796–801) and these sugar residues make a significant contribution to the mosquito toxicity of *B.t. israelensis* (Muthukumar and Nickerson, *App. Environ. Microbiol.*, 1987, 53, 2650–2655).

It has been found that certain strains of *B.t.* naturally transfer or conjugate their native plasmids to other strains of *B.t.* (Gonzalez and Carlton in "Genetic Exchange," U. N. Streips, S. H. Goodgal, W. R. Guild and G. A. Wilson, Eds., 1982, p. 85–95, Marcel Dekker, Inc., New York). However, despite the ability of *B.t.* to naturally conjugate plasmids from one strain to another, the transfer of the 75 mDa mosquito-toxin plasmid from *B.t. israelensis* to a non-*B.t. israelensis* strain of *B.t.* has not been reported. Gonzalez and Carlton (*Plasmid*, 1984, 11, 28–38) have reported the lack of ability to transfer *B.t. israelensis* mosquito-toxin plasmid from *B.t. israelensis* to a non-israelensis strain of *B.t.* However, it is possible to transfer the mosquito-toxin plasmid from a donor *B.t. israelensis* strain to a recipient *B.t. israelensis* strain which had previously lost its 75 mDa mosquito-toxin plasmid.

Jensen et al. (*Current Microbiol.*, 1996, 33, 228–236) have described an aggregation-mediated conjugation system of *B.t. israelensis* wherein a non-toxin plasmid of approximately 130 mDa, designated plasmid pXO16, was tagged with an antibiotic-resistance marker and the antibiotic-tagged, non-toxin plasmid was transferred into various recipient host cells. It should be emphasized that the antibiotic-tagged plasmid pXO16 described by Jensen et al. is known to transfer readily to non-*B.t. israelensis* strains. It is especially emphasized that the *B.t. israelensis* plasmid pXO16 does not carry mosquito-toxin genes. Although the non-toxin 130 mDa plasmid pXO16 of *B.t. israelensis* conjugates readily to non-*B.t. israelensis* strains, the mosquito-toxin 75 mDa plasmid of *B.t. israelensis* has not been found to conjugate into non-*B.t. israelensis* strains as shown by Gonzalez and Carlton (*Plasmid*, 1984, 11, 28–38).

SUMMARY OF THE INVENTION

The present invention relates to the 75 mDa mosquito-toxin plasmid of *B.t. israelensis* which is tagged with an antibiotic-resistance gene. The antibiotic-tagged plasmid is useful in detection of the rare event in which the mosquito-toxin plasmid transfers from a donor strain of *B.t.* into a recipient strain of *B.t.*, the recipient strain being a non-*B.t. israelensis* strain.

The present invention also relates to constructed mosquito-toxic strains of *B.t.* which are non-*B.t. israelensis* strains and which contain the 75 mDa mosquito-toxin plasmid of *B.t. israelensis*. The mosquito-toxic strains are constructed by natural conjugation in which the antibiotic-tagged mosquito-toxin plasmid of *B.t. israelensis* is transferred from a donor strain into a non-israelensis recipient strain of *B.t.* It is within the scope of this invention to use other means, such as electroporation, to introduce the antibiotic-tagged, 75 mDa *B.t. israelensis* toxin-plasmid into recipient strains. Recipient strains have useful properties such as reduced spore numbers or improved ability to produce mosquito-toxic proteins compared with wild-type *B.t. israelensis*.

DETAILED DESCRIPTION OF PREFERRED EMBODIMENTS

The present invention relates to an antibiotic-tagged mosquito-toxin plasmid of approximately 75 mDa size of *B.t. israelensis*. The native *B.t. israelensis* mosquito-toxin plasmid of 75 mDa does not carry an antibiotic-tag and thus the present invention describes one method of adding an antibiotic-tag to the mosquito-toxin plasmid.

The present invention describes a novel method of overcoming the problem of detecting the very low rate of plasmid conjugation of the 75 mDa mosquito-toxin *B.t. israelensis* plasmid by providing a selectable antibiotic-resistance marker on the *B.t. israelensis* mosquito-toxin plasmid. The selectable antibiotic marker permits detection of the rare transfer of the *B.t. israelensis* mosquito-toxin plasmid from a donor cell into a non-israelensis recipient cell even when such a transfer occurs only once in a mixture of many thousands of donor and recipient cells.

The advantage of the present invention is that it permits the construction of non-*B.t. israelensis* strains of bacteria that have the complete 75 mDa mosquito-toxin plasmid of *B.t. israelenesis* and the constructed strains have equivalent mosquito toxicity as wild-type *B.t. israelensis*. In addition, the constructed strains have improved properties compared with *B.t. israelensis* as described in Examples 2, 3, 4 and 5.

According to the present invention mosquito-toxic strains of *B.t.* are constructed by the natural process of plasmid conjugation. The process of plasmid conjugation occurs when cells from two different strains of bacteria are combined and one or more plasmids are transferred from one of the bacteria strains, called the donor strain, to the second bacteria strain, called the recipient strain. Other means of introducing antibiotic-tagged plasmids into cells are well known in the art. For example, the technique of electroporation involves passing an electric current through a mixture of cells and antibiotic-tagged plasmids such that the membranes of the cell become permeable and a certain fraction of the cells receive the plasmid. The well known technique of introducing plasmids into cells by electroporation is described by Belliveau and Trevors (*App. Environ. Microbiol.*, 1989, 55, 1649–1652).

It is within the scope of the present invention that the 75 mDa mosquito toxin plasmid of *B.t. israelensis* be tagged with an antibiotic marker by means known in the art other than the method described in Example 1. For example, the antibiotic tag could be attached to the mosquito-toxin plasmid by homologous DNA recombination. In the method of homologous recombination, a portion of DNA from 75 mDa mosquito-toxin plasmid is cloned into a "suicide" plasmid vector (i.e., a vector unable to replicate in *B.t.* but capable of replicating in another organism such as *Escherichia coli*). The vector contains an antibiotic resistance gene that becomes active when introduced into *B.t.* Introduction, by electroporation, of such a vector containing a portion of the mosquito-toxin plasmid DNA and a selectable antibiotic-resistance marker into *B.t. israelensis*, followed by selection for antibiotic resistance, results in integration, by homologous DNA recombination, of the vector plus antibiotic marker into the mosquito-toxin plasmid of *B.t. israelensis*, resulting in an antibiotic-tagged mosquito toxin plasmid.

Although the *B.t.* crystal toxin gene designations have recently been revised (Crickmore et al., *Microbiol. Molec. Biol. Rev.*, 1998, 62, 807–813), for clarity, the former designations for *B.t. israelensis* crystal toxin will be used for discussion.

EXAMPLES

Example 1

Construction of *B.t. Israelensis* Strain EG12341 Containing an Antibiotic-tagged Mosquito-toxin Plasmid.

In this example a transposon was used to tag the mosquito-toxin plasmid of *B.t. israelensis* with an antibiotic-resistance marker. The wild-type, natural *B.t. israelensis* strain EG2215 was grown to a vegetative stage and cells were prepared for a standard plasmid electroporation procedure. (See, Bellivear and Trevors, *App. Environ. Microbiol.*, 1989, 55, 1649–1652.) Cells were electroporated with the antibiotic-resistance, transposon vector pEG922. Plasmid pEG922 was originally described by Baum (U.S. Pat. No. 5,441,884). Plasmid pEG922 is carried in E. coli strain EG7669 which is deposited with the ARS Patent Collection (Agricultural Research Culture Collection, Northern Regional Research Laboratory (NRRL), 1815 North University Street, Peoria, IIIL. 61604) under the accession number NRRL B-21068.

Plasmid pEG922 contains a chloramphenicol-resistance gene on one portion of the plasmid and a tetracyline-resistance gene on a transposon portion of the plasmid. A transposon is a small segment of DNA that has the property of moving randomly from one segment of DNA to another segment of DNA, a process termed transposition. Bacteria cells that harbor plasmid pEG922, i.e., cells into which pEG922 has been introduced by electroporation, will be resistant to both tetracycline and chloramphenicol. The tetracyline-resistance gene is contained on a transposon in pEG922 and thus the tetracycline-transposon DNA is capable of moving, or transposing, from pEG922 into random segments of the bacteria cell DNA. This process of transposition can be accelerated by taking advantage of the fact that plasmid pEG922 is temperature-sensitive for replication, i.e., pEG922 can replicate in cells that are grown at 30° C., but pEG922 cannot replicate in cells grown at 41° C. When cells harboring pEG922 are grown at 41° C. in the presence of tetracycline and in the absence of chloramphenicol, the only cells which survive will be those in which the tetracycline-transposon DNA has moved from pEG922, which cannot replicate at 41° C., into some part of the cell DNA , such as the *B.t.* genome or a *B.t.* native plasmid, which can replicate at 41° C.

*B.t. israelensis* EG2215 cells containing pEG922 were diluted in LB medium, dilutions were spread on LB agar plates containing 20 ug/mL tetracycline, and the agar plates were incubated overnight at 41° C. After overnight incubation at 41° C., several colonies had grown on LB agar+ tetracycline. It is thought that in colonies which were able to grow in the presence of tetracycline at 41° C., a transposition event had occurred in which the tetracycline-transposon DNA had moved from the temperature-sensitive plasmid pEG922, which could not replicate or confer tetracycline resistance at 41° C., to another segment of DNA such as the EG2215 genome or one of the native EG2215 plasmids which could replicate at 41° C.

Several colonies that grew at 41° C. in the presence of tetracycline were analysed by a standard gel electrophoresis technique for their complement of native plasmids. (See, Gonzalez et al., *Proc. Natl. Acad. Sci. USA*, 1982, 79, 6951–6955.) The gel electrophoresis technique involves lysing cells from individual colonies with lysozyme and electrophoresing DNA that is released from the cells through an agarose gel. After electrophoresis the gel is stained with ethidium bromide and photographed to reveal the size and number of plasmids present in each bacterial colony. Gel electrophoresis analysis showed that none of the colonies which were able to grow in the presence of tetracycline at 41° C. contained plasmid pEG922. This was expected since pEG922 cannot replicate at 41° C. It is believed that in colonies of *B.t. israelensis* strain EG2215 able to grow at 41° C. in the presence of tetracycline, the transposon-tetracycline DNA had moved from pEG922 into either the EG2215 genome or into one of the eight native plasmids of EG2215. However, gel electrophoresis alone was not sufficient to show whether or not the tetracycline-transposon DNA was located in the cell genome or in one of the eight natural plasmids.

The location of the transposon-tetracycline gene in EG2215 colonies capable of growing at 41° C. in the presence of tetracycline was determined by the standard technique of Southern blot analysis (Southern, *J. Mol. Biol.*, 1975, 98, 503–517). The DNA from the gel electrophoresis experiment described above, i.e., the DNA of EG2215 colonies able to grow at 41° C. in the presence of tetracycline, was transferred from the gel to a nitrocellulose filter and the filter was probed with plasmid pEG922 that had been radioactively labeled by standard methods. After probing, the filter was exposed to x-ray film and the film was examined for the presence of dark bands which indicated the location of the tetracycline-transposon DNA. Alignment of the dark bands on the x-ray film with a photograph of the original plasmid electrophoresis gel allowed the precise determination of the location of the tetracycline-transposon DNA within the DNA of the various tetracycline-resistant colonies. This analysis showed that most of the colonies that were able to grow at 41° C. in the presence of tetracycline contained the tetracycline-transposon DNA either within their genome or within one of the *B.t. israelensis* native plasmids which was not the 75 mDa mosquito toxin plasmid. However, the Southern blot analysis showed that one colony, which was designated EG12341, contained the tetracycline-transposon DNA within the 75 mDa mosquito-toxin plasmid.

EG12341 is *B.t. israelensis* strain EG2215 that contains the tetracycline-transposon DNA on the 75 mDa mosquito-toxin plasmid. It should be noted that EG12341 is resistant to tetracycline, due to the presence of the tetracycline-transposon DNA on the 75 mDa plasmid, but EG12341 is sensitive to other antibiotics such as chloramphenicol and streptomycin.

It is possible that the tetracycline-transposon DNA disrupted one of the mosquito-toxin genes present on the 75 mDa plasmid in strain EG12341. To be useful, strain EG12341 must produce the same complement of mosquito-toxic proteins as wild-type *B.t. israelensis* strain EG2215. To determine whether the tetracycline-transposon gene had disrupted any mosquito-toxin genes on the 75 mDa plasmid strain EG12341 was grown at 30° C. for 3 to 4 days in C2 medium, a medium which promotes spore formation and production of mosquito-toxic crystal proteins. C2 medium is 1% glucose, 0.2% peptone, 0.5% NZ amine-A casein hydrolysate (Sheffield Products), 0.2% yeast extract, 15 mM $(NH_4)_2SO_4$, 23 mM $KH_2PO_4$, 27 mM $K_2HPO_4$, 1 mM $MgSO_4.7H_2O$, 0.6 mM $CaCl_2$, 17 $\mu$M $ZnSO_4.7H_2O$, 17 $\mu$M $CuSO_4.5H_2O$, 2 $\mu$M $FeSO_4.7H_2O$). The crystal proteins produced by the sporulated culture of EG12341 were visualized by a standard protein gel electrophoresis technique, also known as sodium dodecyl sulfate-polyacrylamide gel electrophoresis (SDS-PAGE). The SDS-PAGE procedure involves solubilizing the crystal proteins from a portion of the sporulated culture in standard protein solubilization buffer, electrophoresing the solubilized proteins through a polyacrylamide gel and, after electrophoresis, visualizing the proteins by staining the gel with Coomassie dye. The SDS-PAGE analysis showed that G12341 produced the same number and size of proteins as the wild-type-*B.t. israelensis* strain EG2215. Accordingly, the tetracycline-transposon DNA did not disrupt any mosquito toxin genes on the 75 mDa mosquito-toxin plasmid of strain EG12341.

Example 2

Construction of *B.t. Kurstaki* Strain EG12367 Producing *B.t. Israelensis* Mosquito-toxic Proteins.

The present example describes the construction of a non-*israelensis B.t.* strain that produces *B.t. israelensis* mosquito-toxic proteins. The strain was constructed by transferring the 75 mDa, tetracycline-tagged mosquito-toxin plasmid from *B.t. israelensis* strain EG12341 into the non-*israelensis* strain EG10700. Transfer of the 75 mDa plasmid was attempted by use of the technique of bacterial plasmid conjugation. Bacterial plasmid conjugation is a natural process which occurs when one type of bacteria cell which contains a transferrable plasmid comes into contact with a second cell type that does not contain the plasmid. During cell contact, the plasmid is naturally transferred from the first cell type into the second cell type. Gonzalez and Carlton (Plasmid, 1984, 11, 28–38) have shown that the 75 mDa mosquito-toxin plasmid of *B.t. israelensis* did not transfer to non-*B.t. israelensis* strains at a detectable frequency. In the present invention the 75 mDa mosquito-toxin plasmid of *B.t. israelensis* strain EG12341 is tagged with a tetracycline-resistance gene which permits detection of a rare event in which the mosquito-toxin plasmid is transferred into a non-*B.t. israelensis* recipient strain.

EG10700 is a *kurstaki*-type of B.t and EG10700 does not produce mosquito-toxic proteins. EG10700 was made transiently resistant to chloramphenicol by transforming the chloramphenicol-resistance plasmid pEG853 into EG10700 by the process of electroporation. Plasmid pEG853 serves no function other than to make EG10700 transiently resistant to chloramphenicol. pEG853 remains in the EG10700 transformed cells when the cells are grown in the presence of chloramphenicol, but pEG853 is readily lost from cells when the cells are grown in the absence of chloramphenicol, thus chloramphenicol resistance is transient.

EG10700+pEG853 cell culture (900 $\mu$L), grown to the vegetative state in Luria broth, and 3 $\mu$g/mL of chloramphenicol were mixed with 100 $\mu$L of an EG12341 cell culture that had been grown to the vegetative state in Luria broth and 20 $\mu$g/mL of tetracycline. It had previously been determined that EG12341 cells kill or suppress EG10700 cells when the two cell types are mixed and, therefore, it was necessary to add approximately nine times the number of EG10700+pEG853 cells as EG12341 cells in order to have roughly equal numbers of each cell type after the cells had grown in the presence of each other. After mixing of the cells, 50 μL of the mixture of EG10700+pEG853 cells and EG12341 cells was immediately spotted onto the surface of a Luria agar plate that contained no antibiotic, and the cells were allowed to grow overnight at 30° C. After overnight growth on Luria agar the mixture of cells was scraped from the Luria agar and the cells were suspended in Luria broth. To select for EG10700+pEG853 cells that had received the 75 mDa, tetracycline-tagged mosquito-toxin plasmid from EG12341, 0.1 mL portions of the suspension of EG10700+ pEG853 and EG12341 cells were spread on Luria agar plates containing both 20 μg/mL tetracyline and 3 μg/mL chloramphenicol. To determine the number of EG12341 cells and EG10700+pEG853 cells in the mixture, the cell suspension was diluted 100,000-fold in Luria broth and 0.1 mL of the diluted suspension was spread on Luria agar plates containing only tetracycline (20 μg/mL) and also 0.1 mL of the dilution was spread on Luria agar plates containing only chloramphenicol (3 μg/mL). After overnight growth the colonies on each Luria agar plate were counted. Luria agar plates containing only tetracycline had, on average, 31 tetracycline resistant colonies indicating that there were 31×10e6=3.1×10 e7 cells of EG12341 per mL in the undiluted cell suspension. Luria agar plates containing only chloramphenicol contained on average 67 chloramphenicol resistant colonies indicating that there were 67×10e6=6.7× 10e7 cells of EG10700+pEG853 per mL in the undiluted cell suspension. Luria agar plates containing tetracycline and chloramphenicol had, on average, 8 chloramphenicol- and tetracycline-resistant colonies, suggesting that there were 80 cells of EG10700+pEG853 that had received the 75 mDa tetracycline-tagged plasmid per mL in the undiluted cell suspension.

The plasmid arrays of eight colonies that grew on Luria agar plates containing tetracycline and chloramphenicol were evaluated by the gel electrophoresis method to determine whether these colonies were, in fact, EG10700+ pEG853 containing the 75 mDa, tetracycline-tagged mosquito-toxin plasmid. This analysis showed that all eight colonies were EG10700+pEG853 containing the 75 mDa mosquito toxin plasmid. One of the eight colonies was grown in the absence of chloramphenicol which resulted in the loss of plasmid pEG853 yielding a strain designated EG12367. Therefore, EG12367 is B.t. kurstaki strain EG10700 without pEG853 and contains the 75 mDa, tetracycline-tagged mosquito-toxin plasmid.

The experiments described above demonstrate that the frequency of transfer of the 75 mDa mosquito-toxin plasmid is very low. On average, only one EG10700+pEG853 cell received the 75 mDa mosquito-toxin plasmid for every 800,000 such cells that were exposed to donor cells. Such a low frequency is difficult to detect without the use of an antibiotic-tagged mosquito-toxin plasmid as described in the present invention.

Example 3
Construction of B.t. Kurstaki Strain EG12368 Producing B.t. Israelensis Mosquito-toxic Proteins and Lacking Antibiotic Resistance.

Strain EG12367, described in Example 2, is tetracycline-resistant and chloramphenicol-sensitive. For a constructed bacteria strain to be released into the environment it is desirable that the strain not contain any antibiotic-resistance properties which may have been introduced during the construction of the strain. Therefore, the tetracycline-resistance gene present on the 75 mDa mosquito-toxin plasmid in strain EG12367 was deleted by the following procedure.

EG12367 was electroporated with plasmid pEG948 and chloramphenicol-resistant colonies were selected at 30° C. on Luria agar plates containing chloramphenicol. Plasmid pEG948 was derived directly from plasmid pEG922 by digestion of pEG922 with restriction enzyme BssHII and religation. Digestion of pEG922 with BssHII, followed by religation, resulted in the loss of a portion of the tetracycline gene as well as loss of a portion of the transposon. Therefore, pEG948 contains a deleted, inactive tetracycline resistance gene as well as a deleted, inactive transposon but pEG948 contains an intact chloramphenicol-resistance gene. Like pEG922, plasmid pEG948 confers chloramphenicol resistance and is temperature-sensitive for replication, but pEG948 does not confer tetracycline resistance. The plasmid pEG948 may be purified from B.t. kurstaki EG12136.

After electroporation of EG12367 with pEG948 several chloramphenicol resistant colonies grew at 30° C. on Luria agar plates containing 3 μg/mL chloramphenicol. The chloramphenicol-resistant colonies were streaked onto Luria agar plates and the agar plates incubated at 41° C.

As pEG948 cannot replicate at 41° C., the primary means by which a cell containing pEG948 would be able to grow at 41° C. in the presence of chloramphenicol would be for the entire plasmid pEG948 to integrate, by homologous recombination, into the tetracyline-transposon DNA present on the 75 mDa mosquito toxin plasmid of strain EG12367. Homologous recombination is a natural event whereby a segment of DNA inserts itself into a corresponding homologous segment of DNA. It should be noted that homologous integration of pEG948 into the transposon-tetracycline DNA on the 75 mDa plasmid of EG12367 is not a transposition event as the transposon function of pEG948 has been inactivated by deletion as described above.

Plasmid pEG948 is inserted into the intact, active tetracycline-transposon DNA present on the 75 mDa plasmid of EG12367. This insertion is possible because pEG948 retains a small, deleted portion of the tetracycline-transposon DNA which is homologous with a portion of the full-length tetracycline-transposon DNA on the 75 mDa plasmid. It is well known that homologous integration is reversible. In the absence of selective pressure, i.e., in the absence of chloramphenicol, it was expected that plasmid pEG948 would undergo a reversal of homologous integration, also called excision, in which pEG948 was excized from the tetracycline-transposon DNA on the 75 mDa plasmid. Such an excision event leaves behind one of two possible types of DNA on the 75 mDa plasmid: one type of excision would leave behind the intact tetracycline-transposon DNA, capable of conferring tetracycline-resistance, on the 75 mDa plasmid. The second type of excision would leave behind a partially deleted tetracycline-transposon DNA, that was not capable of conferring tetracycline resistance, on the 75 mDa plasmid.

One chloramphenicol resistant colony of EG12367+ pEG948 was streaked onto Luria agar containing chloramphenicol and incubated at 41° C. to force homologous integration of pEG948 into the tetracycline-transposon DNA on the 75 mDa plasmid. Several colonies which grew at 41° C. on Luria agar containing chioramphenicol were restreaked onto Luria agar plates without chloramphenicol and were incubated at 30° C. to allow for excision and loss of pEG948. Forty-five of the resulting colonies that grew on Luria agar at 30° C. were tested for their ability to grow on Luria agar containing 20 µg/mL tetracycline as well as their ability to grow on Luria agar containing 3 µg/mL chloramphenicol. One colony, designated EG12368, was unable to grow in either the presence of tetracyline or chloramphenicol. Analysis of the plasmid array of EG12368 by gel electrophoresis showed that EG12368 was a derivative of B.t. kurstaki strain EG10700 that contained the 75 mDa mosquito-toxin plasmid. This analysis verified that the tetracycline-transposon DNA on the 75 mDa plasmid of EG12368 had been inactivated by partial deletion.

To determine whether EG12368 produced mosquito-toxic proteins, the strain was grown in C2 sporulation medium and proteins in the sporulated culture were analyzed by SDS-PAGE. This analysis showed that EG12368 produced an identical number and size of mosquito-toxic proteins as the wild-type B.t. israelensis strain EG2215 with the exception that EG12368 produced more of the 130 kDa and 70 kDa proteins than EG2215 as judged by SDS-PAGE.

Therefore, EG12368 is a B.t. kurstaki strain that produces the B.t. israelensis mosquito-toxic proteins, and is immediately derived from EG12367. Furthermore, as EG12368 is obtained upon elimination of antibiotic resistance from EG12367, EG12368 does not contain active tetracycline-resistance or chloramphenicol-resistance genes.

Example 4
Construction of B.t. Kurstaki Strain EG12396 Producing B.t. israelensis Mosquito-toxic Proteins, and having a Reduced Level of Spores.

The present invention describes the construction of non-israelensis strains of B.t. that are toxic to mosquitos. Certain non-israelensis B.t. strains mai have advantageous properties compared with wild-type B.t. israelensis, such as increased production of mosquito-toxic proteins. The present example describes a non-israelensis B.t. strain, i.e., B.t. kurstaki strain, having a reduced spore number.

B.t. spores are formed at the end of vegetative cell growth when nutrients become depleted in the environment of B.t. cells. B.t. spores can persist in the environment for long periods of time and are resistant to killing by UV radiation, chemicals, and heat. For example, heating vegetative B.t. cells at 65° C. for 30 minutes would kill almost 100% of the cells, but only a small percentage of B.t. spores would be killed by similar heating.

In certain areas it is not desirable to apply large numbers of B.t. spores because they would persist in the environment. One area where large numbers of B.t. spores may not be desirable would be the treatment of water with mosquito-toxic B.t. to control mosquito larvae.

The method of the present invention introduces the tetracycline-tagged mosquito-toxin B.t. israelensis plasmid into strain EG7644. EG7644 is a B.t. kurstaki strain that does not produce insecticidal crystal proteins and EG7644 is defective in its ability to form heat-resistant spores.

The tetracycline-tagged, 75 mDa B.t. israelensis mosquito-toxin plasmid was introduced into the sporulation-deficient B.t. kurstaki strain EG7644 in a manner similar to that described for the construction of the mosquito-toxic strain EG12367 in Example 2. B.t. kurstaki strain EG7644 was made transiently resistant to chloramphenicol by using electroporation to introduce the chloramphenicol-resistance plasmid pEG889 into EG7644. pEG889 functions only to make EG7644 cells transiently resistant to chloramphenicol. EG7644+pEG889 cells at a vegetative stage of growth were mixed with vegetative EG12367 cells which contained the tetracycline-tagged 75 mDa mosquito-toxin plasmid as described in Example 2. A 50 µL portion of the mixture was pipetted onto Luria agar and allowed to grow overnight. After growth overnight on LB agar, the mixture of EG7644+pEG889 cells and EG12367 cells was suspended in Luria broth and 0.1 mL portions of the suspension were spread on Luria agar containing 20 µg/mL tetracycline plus 3 µg/mL chloramphenicol. Several colonies that grew on the Luria agar containing tetracycline plus chloramphenicol were analyzed for their array of plasmids by the gel electrophoresis procedure which showed that one colony, designated strain EG12390, was a derivative of B.t. kurstaki strain EG7644 (sporulation deficient) and that EG12390 contained the 75 mDa, tetracycline-tagged B.t. israelensis mosquito-toxin plasmid. Strain EG12390 was grown in the absence of chloramphenicol to allow loss of plasmid pEG889. One colony that was chloramphenicol-sensitive due to the loss of pEG889 was designated EG12391. EG12391 is a sporulation-deficient, B.t. kurstaki strain containing the tetracycline-tagged, B.t. israelensis mosquito-toxin plasmid.

The tetracycline-tag was deleted from EG12391 in the same manner as described for the deletion of the tetracycline-tag from EG12367 in Example 3. EG12391 was transformed by electroporation with plasmid pEG948. The transformed cells were grown in Luria broth at 41° C. in the presence of chloramphenicol, and the cells were then grown in Luria broth at 30° C. in the absence of chloramphenicol. After growth in the absence of chloramphenicol, individual colonies were tested for sensitivity to chloramphenicol as well as tetracycline. One chloramphenicol-sensitive and tetracycline-sensitive colony was designated EG12396. Gel analysis showed that EG12396 contained the 75 mDa mosquito-toxin plasmid.

EG12396 was grown in C2 sporulation medium at 30° C. for three to four days. The number of heat-resistant spores was determined by heating a portion of the EG12396 culture at 65° C. for 30 minutes. The heated culture was diluted and dilutions were plated on Luria agar plates. The Luria agar plates were incubated at 30° C. for 16 hours to allow viable cells to grow into colonies, and the number of colonies on the agar plates were counted. Counts were multiplied by the dilution factor to obtain the number of heat-resistant cells (spores) in the original EG12396 culture. This analysis showed that the heated EG12396 culture contained less than 5 heat-resistant spores per milliliter of culture. In contrast, an identically-treated culture of wild-type B.t. israelensis strain EG2215 contained approximately 4×10e8 heat-resistant spores per milliliter. Thus, EG12396 produces less than one-hundred millionth the number of heat resistant spores as the sporulation-proficient B.t. israelensis strain EG2215.

Mosquito-toxic proteins produced by the EG12396 culture were evaluated by the SDS-PAGE technique. SDS-PAGE analysis showed that the EG12396 culture produced the same number and size of mosquito-toxic proteins as the identically grown B.t. israelensis strain EG2215.

In summary, EG12396 is a B.t. kurstaki strain that produces the complete array of B.t. israelensis mosquito-toxic proteins. EG12396 produces less than one-hundred millionth the number of heat-resistant spores as wild-type B.t. israelensis. Therefore, EG12396 is useful in the control of mosquitos especially in environmental settings where reduced spores are desirable.

Example 5
Construction of B.t. Jegathesan strain EG12410 Producing Mosquito-toxic Proteins of both B.t. Jegathesan and B.t. israelensis.

B.t. jegathesan is a mosquito-toxic strain whose toxin proteins are significantly different from those of B.t. israelensis (Kawalek et al., *Appl. Environ. Microbiol.*, 1995, 61, 2965–2969). Using the methods described in the present invention the tetracycline-tagged, *B.t. israelensis* mosquito-toxin plasmid was introduced into the *B.t. jegathesan* strain yielding a strain that produced both *jegathesan*-type mosquito-toxic proteins as well as *israelensis*-type mosquito-toxic proteins. Such a strain would be useful in having a broader range of mosquito toxicity to several species of mosquitos compared with *B.t. jegathesan* or *B.t. israelensis* alone.

The antibiotic-tagged 75 mDa mosquito-toxin *B.t. israelensis* plasmid of the present invention was used to construct the novel *B.t. jegathesan* strain EG12410 that produces both *B.t. jegathesan* proteins and *B.t. israelensis* proteins. EG12410 was constructed by the following procedure. *B.t. jegathesan* strain T28A001 was obtained from the Pasteur Institute Culture Collection (25 rue du Docteur Roux, 75724 Paris Cedex 15), and was designated strain EG2307 for purposes of record keeping. EG2307 was made transiently resistant to chloramphenicol by using electroporation to introduce the chloramphenicol-resistance plasmid pEG853 into EG2307. EG2307+pEG853 vegetative cells were mixed with vegetative cells of a chloramphenicol-sensitive *B.t.* strain that contained the tetracycline-tagged *B.t. israelensis* mosquito-toxin. A 50 uL portion of the cell mixture was pipetted onto Luria agar, and the cells were allowed to grow overnight. After growth overnight on LB agar the cell mixture was suspended in Luria broth and 0.1 mL portions of the suspension were spread on Luria agar containing 20 $\mu$g/mL tetracycline plus 3 $\mu$g/mL chloramphenicol. Several colonies that grew on the Luria agar containing tetracycline and chloramphenicol were analyzed for their array of plasmids by the plasmid gel procedure which showed that one colony, designated EG12410, consisted of strain EG2307 (*B.t. jegathesan*) that contained the 75 mDa, tetracycline-tagged mosquito-toxin plasmid of *B.t. israelensis*. The plasmid gel analysis showed that EG12410 was missing a plasmid of approximately 70 mDa that was normally present in *B.t. jegathesan* strain EG2307.

Strains EG12410 (*B.t. jegathesan* containing the 75 mDa, tetracycline-tagged mosquito toxin plasmid of *B.t. israelensis*), EG2307 (wild-type *B.t. jegathesan*) and EG2215 (wild-type *B.t. israelensis*) were grown in C2 sporulation medium at 30° C. for 3 to 4 days. After growth, the sporulated cultures were examined by SDS-PAGE analysis for the production of proteins. As expected, EG2215 produced proteins of approximately 130 kD, 70 kD and 28 kD representing the mosquito-toxic crystal proteins of *B.t. israelensis*. EG2307 produced crystal proteins of approximately 77 kD, 74 kD, 70 kD, 55 kD, 28 kD and 10 kD. It has not yet been determined which of the *B.t. jegathesan* proteins are responsible for the strain's mosquitocidal activity. EG12410 produced proteins of approximately 130 kD, 77 kD, 74 kD, 70 kD, and 28 kD. Thus, EG12410 produced a combination of *B.t. israelensis* proteins and *B.t. jegathesan* proteins, although some of the proteins produced y EG12410 were in lesser amounts than proteins produced by *B.t. jegathesan* EG2307 and *B.t. israelensis* EG2215.

Example 6
Toxicities of Constructed Strains to Mosquito Larvae.

Constructed *B.t.* strains EG12341, EG12368 and EG12396, described in Examples 1, 3 and 4, respectively, were grown in C2 sporulation medium for three to four days at 30° C. to allow spore formation and crystal protein production. Wild-type *B.t. israelensis* strain EG2215 was grown in an identical manner. Sporulated cultures were harvested by centrifugation and were resuspended with one-fifth volume of deionized water. Resuspended cultures were diluted in deionized water yielding eight dilutions ranging from approximately 0.1 nanoliters (nL) of resuspended culture per milliliter (mL) of deionized water to 4 nL of resuspended culture per milliliter of deionized water. One mL of each dilution was transferred to a plastic cup and 10 Aedes aegypti four-day-old mosquito larvae were added to each cup. After 24 hours the numbers of live and dead larvae were determined in each cup. Standard probit analysis (Daum, *Bull. Entomol. Soc. Am.*, 1970, 16, 10–15) was used to calculate the concentration of each resuspended *B.t.* culture, in nL of culture per mL of deionized water, producing 50% larvae mortality. The results are shown in Table 1.

TABLE 1

| Concentration of B.t. cultures causing 50% mortality to mosquito larvae | |
|---|---|
| Culture | $LC_{50}{}^a$ |
| EG2215 | 1.2 |
| EG12341 | 1.1 |
| EG12368 | 1.1 |
| EG12396 | 1.0 |

$^a$ = $LC_{50}$ is nanoliters of harvested and resuspended B.t. culture per milliliter of deionized water causing 50% mortality after 24 hours of 4 day old *Aedes aegypti* mosquito larvae.

These results demonstrate that the constructed, non-*B.t. israelensis* strains EG12341, EG12368 and EG12396 have comparable mosquitocidal activities as wild-type *B.t. israelensis* strain EG2215. These novel strains represent the first reported non-*B.t. israelensis* constructed strains that have similar mosquitocidal activities as wild-type *B.t. israelensis*.

Example 7
Deposited Strains.

The following constructed strains have been deposited with the ARS Patent Collection (Agricultural Research Culture Collection, Northern Regional Research Laboratory (NRRL), 1815 North University Street, Peoria, Ill. 61604) under the terms of the Budapest Treaty.

| Bacterial Strain | Relevant Plasmid | NRRL Number |
|---|---|---|
| B.t. *israelensis* EG12341 | tetracycline-tagged 75 mDa mosquito-toxin | B-30161 |
| B.t. *kurstaki* EG1236 | 75 mDa mosquito-toxin | B-30164 |
| B.t. *kurstaki* EG12396 | 75 mDa mosquito-toxin plasmid | B-30163 |
| B.t. *jegathesan* EG12410 | tetracycline-tagged 75 mDa mosquito-toxin | B-30160 |
| B.t. *kurstaki* EG12136 | pEG948, deleted tetracycline and deleted transposon | B-30162 |
| *Escherichia coli* EG7669 | pEG922, intact tetracycline and intact transposon | B-21068 |

What is claimed is:

1. A constructed *B.t. israelensis* strain containing a *B.t. israelensis* mosquito-toxin plasmid of approximately 75 mDa wherein the toxin plasmid has been tagged with an antibiotic-resistance marker.

2. The strain of claim 1 wherein said antibiotic is tetracycline.

3. The strain of claim 1 comprising *B.t. israelensis* EG12341 containing the *B.t. israelensis* mosquito-toxin plasmid of approximately 75 mDa tagged with an antibiotic-resistance marker.

4. The strain of claim 3 wherein said antibiotic is tetracycline.

5. A constructed *B.t.* strain which is not *B.t. israelensis* but which contains the mosquito-toxin plasmid of approximately 75 mDa from *B.t. israelensis*.

6. The strain of claim 5 comprising *B.t. kurstaki* EG12368.

7. The strain of claim 5 comprising sporulation-deficient *B.t. kurstaki* EG12396.

8. The strain of claim 5 comprising *B.t. jegathesan* EG12410.

9. A constructed *B.t. israelensis* strain EG12341 containing a *B.t. israelensis* mosquito-toxin plasmid of approximately 75 mDa tagged with an antibiotic-resistance marker.

10. The strain of claim 9 wherein said antibiotic is tetracycline.

11. A constructed *B.t.* strain which is not *B.t. israelensis* but which contains a mosquito-toxin plasmid of approximately 75 mDa from *B.t. israelensis* strain EG12341 containing the mosquito-toxin plasmid of approximately 75 mDa tagged with an antibiotic resistance marker.

12. The strain of claim 11 wherein the constructed *B.t.* strain is a *B.t. kurstaki* strain.

13. The strain of claim 11 comprising *B.t. kurstaki* EG12367.

14. The strain of claim 11 comprising sporulation-deficient *B.t. kurstaki* EG12390.

15. The strain of claim 11 comprising *B.t. jegathesan* EG12410.

16. The strain of claim 11, from which the antibiotic resistance marker has been removed in the constructed *B.t.* strain which is not *B.t. israelensis*.

17. The strain of claim 16 comprising *B.t. kurstaki* EG12368.

18. The strain of claim 16 comprising sporulation-deficient *B.t. kurstaki* EG12396.

19. The strain of claim 16 comprising *B.t. jegathesan* EG12410.

* * * * *